United States Patent [19]

Pohndorf

[11] Patent Number: 4,590,949
[45] Date of Patent: May 27, 1986

[54] NEURAL STIMULATING LEAD WITH STABILIZING MECHANISM AND METHOD FOR USING SAME

[75] Inventor: Peter J. Pohndorf, Miami Shores, Fla.

[73] Assignee: Cordis Corporation, Miami, Fla.

[21] Appl. No.: 667,228

[22] Filed: Nov. 1, 1984

[51] Int. Cl.⁴ ............................................. A61N 1/04
[52] U.S. Cl. .................................................. 128/785
[58] Field of Search ........................ 128/784, 785, 786

[56] References Cited

U.S. PATENT DOCUMENTS

| | | | |
|---|---|---|---|
| 2,022,065 | 11/1935 | Wappler | 174/89 |
| 3,516,412 | 6/1970 | Ackerman | 128/418 |
| 3,754,555 | 8/1973 | Schmitt | 128/785 |
| 3,814,104 | 6/1974 | Irnich et al. | 128/418 |
| 3,835,864 | 9/1974 | Rasor et al. | 129/419 P |
| 3,844,292 | 10/1974 | Bolduc | 128/418 |
| 3,902,501 | 9/1975 | Citron et al. | 128/418 |
| 3,976,082 | 8/1976 | Schmitt | 128/418 |
| 4,033,357 | 7/1977 | Helland et al. | 128/418 |
| 4,057,067 | 11/1977 | Lajos | 128/418 |
| 4,217,913 | 8/1980 | Dutcher | 128/785 |
| 4,236,529 | 12/1980 | Little | 128/785 |
| 4,257,428 | 3/1981 | Barton et al. | 128/785 |
| 4,269,198 | 5/1981 | Stokes | 128/785 |
| 4,285,347 | 8/1981 | Hess | 128/785 |
| 4,374,527 | 2/1983 | Iversen | 128/786 |
| 4,409,994 | 10/1983 | Doring | 128/785 |
| 4,414,983 | 11/1983 | Dickhudt et al. | 128/785 |
| 4,419,819 | 12/1983 | Dickhudt et al. | 128/785 |

*Primary Examiner*—William E. Kamm
*Attorney, Agent, or Firm*—Henry W. Collins; Thomas R. Vigil

[57] ABSTRACT

A neural stimulating lead including a stabilizing mechanism. The stabilizing mechanism comprises two pairs of parallel laterally projecting vanes and an extendible tine adapted to be extended to apply pressure against a dorsal surface of a vertebrum to force and hold an electrode assembly of the neural stimulating lead against a spinal cord. The tine is extendible through a port in the electrode surface from a retracted position within the lead body to an extended position by pulling on an actuating cable which is attached at one end to the tine and which has its other end extending from a connector portion on a proximal end of the lead.

20 Claims, 8 Drawing Figures

NEURAL STIMULATING LEAD WITH STABILIZING MECHANISM AND METHOD FOR USING SAME

BACKGROUND OF THE INVENTION

1. Field of the Invention

The present invention relates to a neural stimulating lead including a stabilizing mechanism. More specifically, tne present invention relates to a stimulating lead incuding a stabilizing mechanism which is adapted for movement within an epidural space of a vertebrum to stabilize the positioning of an electrode of the lead at a desired location along the spinal cord traversing the vertebrae of the spine.

2. Description of the Prior Art

Heretofore, stimulating leads for use in spinal cord stimulation have had a tendency to migrate after placement. The migration has a considerable effect on stimulation no matter how miniscule the migration is. In this respect, migration of a stimulating lead will lead to poor electrical contact of the electrode with the spinal cord or will lead to stimulation of an improper area of the spinal cord which will negate the effect required, such as stimulation of a precise area to alleviate pain.

To overcome such migration, various solutions have been proposed, such as, for example, button electrodes for S-shaped leads. Examples of some of these proposed solutions are disclosed in the following U.S. Patents:

The Ackerman U.S. Pat. No. 3,516,412 discloses a bipolar electrode which is fed through a needle to a desired point of lodgement and, when the needle is withdrawn, the electrode end bends to an angle of up to 90° C. to provide secure placement of a tip of the electrode against tissue.

The Hess U.S. Pat. No. 4,285,347 discloses a neural electrode lead with stabilizing structure. The stabilizing structure here is in the form of lateral expandable loop elements.

The Dickhudt et al. U.S. Pat. No. 4,414,986 discloses a biomedical stimulation lead which has perpendicularly extending tines located at a tip of a lead body. Further, the lead body, proximal to the electrode, is provided with a helical configuration to add another stabilizing element which stabilizes the electrode during the period immediately after implantation.

The Dickhudt et al. U.S. Pat. No. 4,419,819 discloses a biomedical lead with lobed lead anchor. The anchor comprises a sleeve which is slit in a direction parallel to the axis of the lead body and when the tubing is compressed, the slit portions expand into lobes to stabilize the position of a lead electrode therein.

As will be described in greater detail hereinafter, the lead of the present invention includes a stabilizing mechanism which comprises a tine that is movable from a retracted position to an extended position for securing an electrode against spinal cord tissue. Further, the tine is retractable when it is desired to remove the lead.

SUMMARY OF THE INVENTION

According to the invention there is provided a neural stimulating lead comprising a hollow lead body having a proximal end and a distal end portion which has a side port therein, a distal electrode assembly mounted in said distal end portion and including a sleeve electrode, a stimulator connector mounted at said proximal end of said lead body, a wire conductor connected between said sleeve electrode and said stimulator connector and an active fixation stabilizng mechanism situated in said distal end portion and comprising stiff, but flexible, laterally projecting, vertebrum engaging means and extendable/retractable, dorsal stabilizing means comprising a stiff, but flexible, elongate member which has a proximal inner end and a distal, free end and which is movable transversely of said vertebrum engaging means through said port between a retracted position and an extended position where said free end bears against a dorsal wall of a vertebrum for anchoring said lead within an epidural space of a vertebrum of a spine, said elongate member being positioned entirely within the hollow lead body in its retracted state, and being extendible outwardly from its position within the hollow lead body through said port.

Further according to the invention there is provided a method of using a neural stimulating lead with an active fixation stabilizing mechanism comprising the steps of: feeding a lead comprising a hollow lead body having a proximal end and a distal end portion which has a side port therein, a distal electrode assembly mounted in said distal end portion and including a sleeve electrode, a stimulator connector mounted at said proximal end of said lead body, a wire conductor connected between said sleeve electrode and said stimulator connector and an active fixation stabilizing mechanism situated in said distal end portion and comprising, stiff but flexible, laterally projecting, vertebrum engaging means and extendable/retractable, dorsal stabilizing means comprising a stiff, but flexible, elongate member which has a proximal inner end and a distal end and which is movable transversely of said vertebrum engaging means through said port between a retracted position and an extended position where said free end bears against a dorsal wall of a vertebrum for anchoring said lead within an epidural space of a vertebrum of a spine, said elongate member being positioned entirely within the hollow lead body in its retracted state, and being extendible outwardly from its position within the hollow lead body through said port, through an incision and into an epidural space of foramen of a vertebrum in such a manner that said laterally extending vertebrum engaging means lie in a horizontal plane when a patient is supine and such that said elongate member can be moved upwardly within the foramen; positioning said sleeve electrode in a proper position; and once said sleeve electrode is positioned, moving said elongate member an appropriate distance upwardly and outwardly of said lead body to place the distal free end of said elongate member at a position where said distal end engages and anchors itself against a dorsal wall of the vertebrum within which is it positioned.

DESCRIPTION OF THE PREFERRED EMBODIMENT

Figure 1:
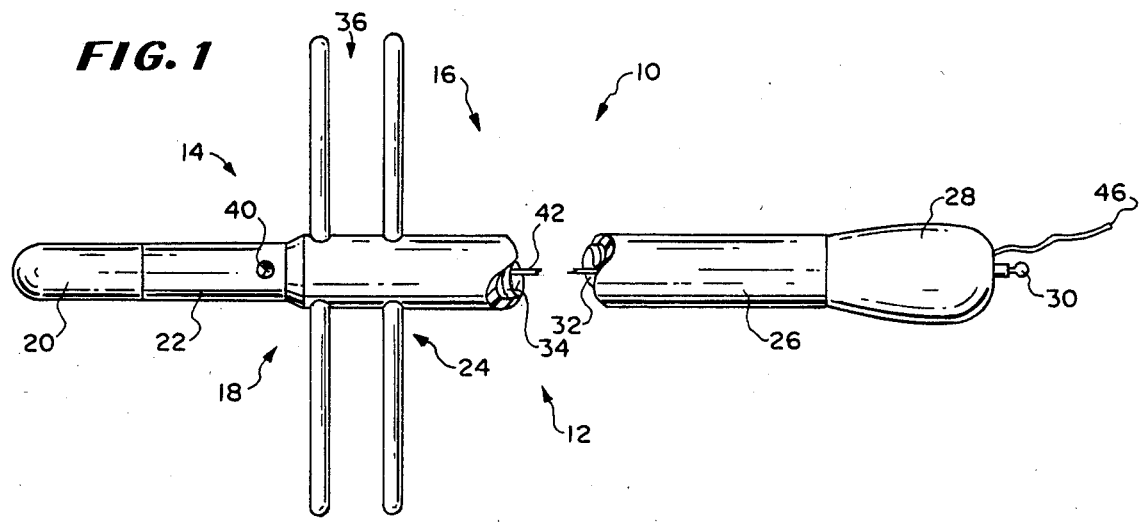
FIG. 1 is a top plan view of the lead including stabilizing mechanism of the present invention therein with portions broken away.

Referring now to the drawings in greater detail, there is illustrated in FIG. 1 a neural stimulating lead 10. As shown, the lead 10 includes a body 12 having a distal end portion 14 and a remaining proximal portion 16. The distal end portion 14 has an electrode assembly 18 mounted thereon which includes a distal lead tip 20, a sleeve electrode 22 and a stabilizing mechanism 24 associated with the sleeve electrode 22 with the remaining portion of the lead body 12 being referred to and identified as the proximal portion 16.

Attached to a proximal end 26 of the proximal portion 16 is a stimulator connector 28 from which a terminal pin 30 extends. The connector 28 provides simple means for connecting the lead 10 to a source of stimulating current.

The lead body 12 is hollow throughout and has extending through a lumen 32 thereof a coiled conductor 34 which is electrically connected between the sleeve electrode 22 and the connector 28. The sleeve electrode 22 may be made of a platinum-iridium material or stainless steel while the distal lead tip 20 and proximal portion 16 are made of a silastic material or polyurethane.

The lead body 12 is formed by molding the distal lead tip 20 and the proximal portion 16 onto the sleeve electrode 22.

Further as shown in FIG. 1, the stabilizing mechanism 24 comprises two pairs 36, 38 of vanes or tines which extend laterally from the lead body 12 just proximal to the sleeve electrode 22.

As will be described in further detail in connection with the description of FIG. 2, the stabilizing mechanism 24 is also provided with a dorsally extending tine 29 which exits a tine port 40 to provide the stabilizing mechanism 24 with anterior-posterior stability while the vane pairs 36, 38 provide stabilization against lateral movement. The tine 39 is activated by an actuating cable 42, the proximal end 46 of which exits the proximal end 26 of the lead 10.

The vanes pairs 36, 38 of the stabilizing mechanism 24 are molded into or formed as a part of the proximal portion 16 which is made of a silastic material or polyurethane. Also, the tine 39 is made of polyurethane or of a silastic material utilized in the formation of the lead body 12.

Figure 6:
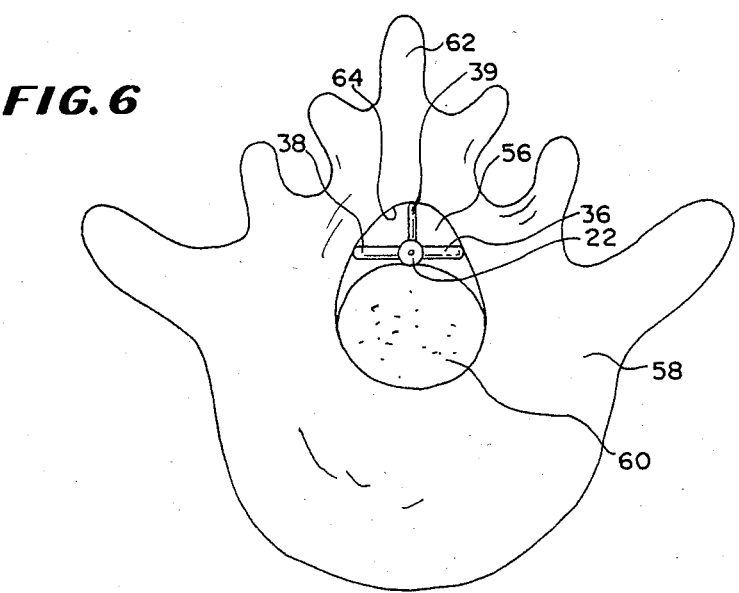
FIG. 6 is a radial cross sectional view through a vertebrum and through the lead after the lead has been properly positioned within an epidural space of the vertebrum and the dorsal tine has been moved to the extended position thereof.

The sleeve electrode 22 is machined to provide the port 40 therein, on what will become the dorsal surface of the lead 10 upon its placement. The tine 39 exits this port 40 from a position within the lumen 32 of the lead body 12 when activated to secure itself against a dorsal wall of a vertebrum within which it is placed (FIG. 6).

Figure 2:
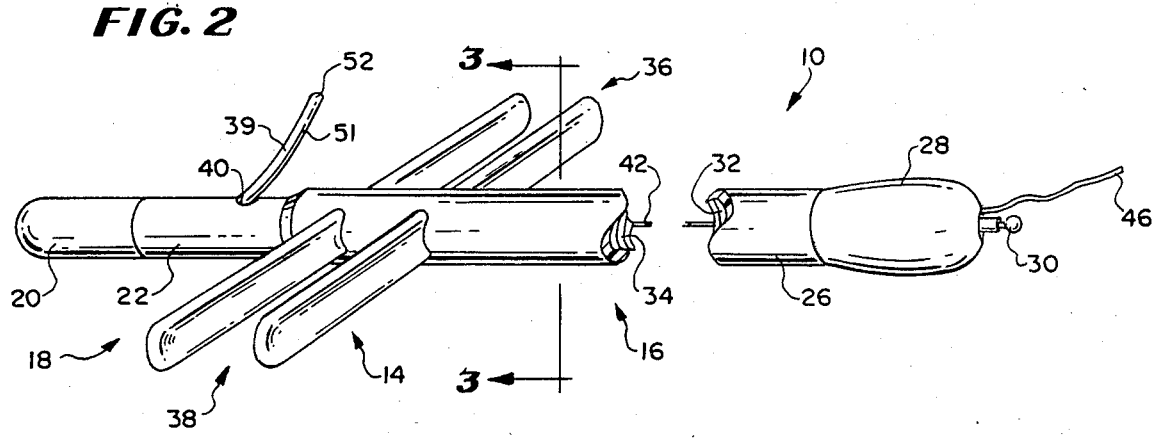
FIG. 2 is a side perspective view of the lead shown in FIG. 1 with portions broken away and shows a doral tine of the stabilizing mechanism in an extended position.

Referring now to FIG. 2, the laterally projecting vane pairs 36, 38 are transverse wing-like structures and are utilized for lateral stabilization of the electrode assembly 18 once the assembly 18 is positioned within a vertebrum. As illustrated, the extendable tine 39 has a slightly curved portion 51 adjacent its distal tip 52 and which is adapted to extend through the port 40. The tine 39, when extended into the epidural space of a vertebrum (FIG. 6), will force the undersurface of the sleeve electrode 22 against the spinal cord to assure good electrical contact therewith as well as providing for stabilization of the sleeve electrode 22 against dorsal movement away from the spinal cord as will be described in greater detail in connection with the description of FIG. 6.

Figure 3:
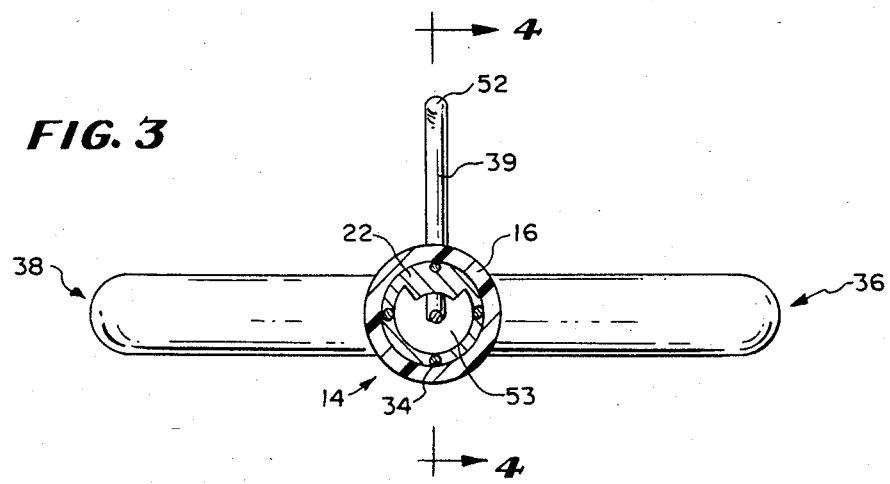
FIG. 3 is a radial sectional view of the lead shown in FIG. 2 and is taken along line 3—3 of FIG. 2.

Turning now to FIG. 3, the vane pairs 36, 38 are winglike flattened projections which lie perpendicularly across the horizontal plane of the electrode assembly 18 when it is positioned within a supine patient, with each pair lying approximately in the horizontal plane.

The dorsal tine 39 projects from its position within the lumen 32 of the distal end portion 14 in a plane which is radially perpendicular to the horizontal plane in which the vane pairs 36, 38 are positioned and the tine 39 will be somewhat angled, caudally or cephalically, depending on the direction of entry of the lead 10.

Figure 4:
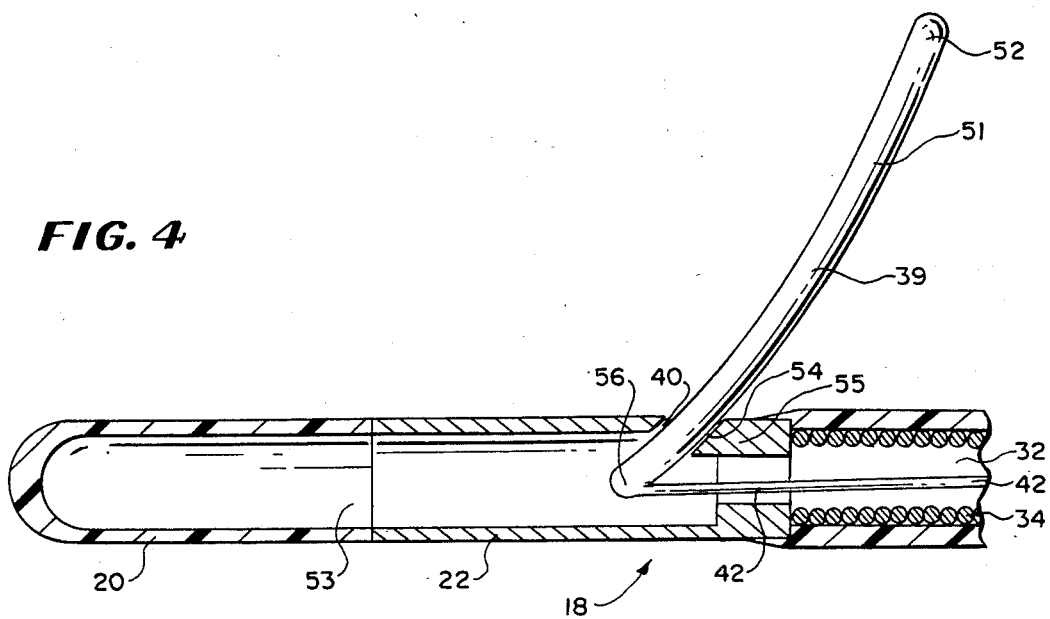
FIG. 4 is an axial cross-sectional view of a distal portion of the lead shown in FIG. 3, is taken along line 4—4 of FIG. 3 and shows the dorsal tine in its extended position.

Referring now to FIG. 4, there is illustrated therein an enlarged axial cross-sectional view of the distal end portion 14 of the lead 10 of the present invention. As illustrated, when activated, the tine 39 projects outwardly from an inner space or lumen 53 within the distal end portion 14 and more specifically within sleeve electrode 22 through the port 40 on the dorsal surface of the electrode 22 of the lead 10. The port 40 is machined in the sleeve electrode 22 which is provided within the beveled portion 54 of a shoulder 55 adjacent the port 40 against which the distal tip 52 of the tine 39 abuts and slides upwardly as it is extended from its retracted position within the lumen 32 of the distal end portion 14. The shoulder 55 acts as a stop member as well to keep the tine 39 from becoming disassociated from the lead 10.

In this respect, when the tine 39 is extended by pulling on the proximal end 46 of the actuating cable 34 extending from the proximal end of the lead 10, the distal end 52 of the tine 39 is pulled proximally and this movement causes the proximal end 42 of the tine 39 to slide upwardly and subsequently outwardly from its position within the lumen 32 along the beveled portion 54 of the shoulder 55. This movement of the tine 39 from its position within the lumen 32 is stopped when the distal end 52 of the tine 39 abuts a dorsal spine of the vertebrum within which it is positioned. Also, if the epidural space within the vertebrum proves to be of greater height than the length of the tine 39, the tine 39 will not become disassociated from the lead 10 by reason of the beveled portion 54 of shoulder 55 becoming wedged against the junction formed where a proximal end 56 of the tine 39 is attached to the actuating cable 34.

The tine 39 may be provided with various lengths to accomodate various dimensions of an epidural space. For example, if placed within an infant or child, the tine 39 would only need to be extended a very short distance until it would abut the dorsal spine of the vertebrum, whereas in a larger patient, it could be extended its entire length without fear of having the tine 39 become disassociated from the lead 10 and being left within the vertebrum after removal of the lead 10.

Figure 5:
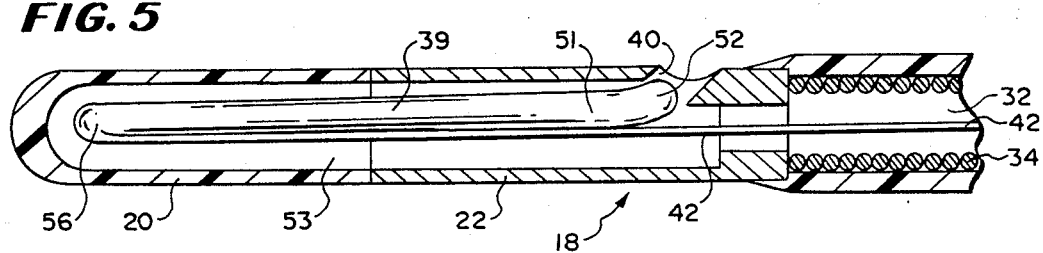
FIG. 5 is an axial cross sectional view similar to the view shown in FIG. 4 and shows the dorsal tine in a retracted position.

Turning now to FIG. 5, which illustrates the tine 39 in its retracted position, it will be seen that the tine 39 is provided with the slightly curved portion 51 configuration to ensure the abutment of its distal tip 52 against the beveled shoulder 44 of the port 40. Also, the length of the tine 39 is limited by the length provided to the distal portion 14, and sleeve electrode 22 and the longitudinal position along the sleeve electrode 22 at which the tine port 40 is machined.

Referring now to FIG. 6, once the sleeve electrode 22 of the lead 10 is positioned within an epidural space 56 of a vertebrum 58, with the electrode portion 22 and vanes 36, 38 lying in a horizontal plane along a spinal cord 60 when the dorsum 62 of the vertebrum 58 is facing upwardly, as when a patient is lying supine, the actuating cable 34 is pulled slightly until the tine 39 is forced against the dorsal wall 64 of the epidural space 56 to force and hold the undersurface of the sleeve electrode 22 against the spinal cord 60. The tine 39 not only ensures good electrical contact between the spinal cord 60 and the sleeve electrode 22 of the lead 10 but also stabilizes the position of the sleeve electrode 22 against slipping longitudinally within the epidural space 56 by forming a wedge against the dorsal wall 64.

As long as tension is maintained on the actuating cable 34, the tine 39 will remain extended.

When it is desired to remove the lead 10 from its position within the vertebrum 58, tension is released from the actuating cable 42, and the tine 39 becomes dislodged from its position against the dorsal wall 64 of the vertebrum 58, allowing for simple removal of the lead 10.

As described above, the lead 10 of the present invention with stabilizing mechanism, has a number of advantages, some of which have been described above and others of which are inherent in the invention. Also, modifications can be made to the lead 10 with stabilizer mechanism 24 of the invention without departing from the teachings of the present invention. Accordingly, the scope of the invention is only to be limited as necessitated by the accompanying claims.

I claim:

1. A neural stimulating lead comprising a hollow lead body having a proximal end and a distal end portion which has a side port therein, a distal electrode assembly mounted in said distal end portion and including
   a sleeve electrode, a stimulator connector mounted at said proximal end of said lead body, a wire conductor connected between said sleeve electrode and said stimulator connector and an active fixation stabilizing mechanism situated in said distal end portion and comprising stiff, but flexible, laterally projecting, vertebrum engaging means and
   extendable/retractable, dorsal stabilizing means comprising a stiff, but flexible, elongate member which has a proximal inner end and a distal, free end and which is movable transversely of said vertebrum engaging means through said port between a retracted position and an extended position where said free end bears against a dorsal wall of a vertebrum for anchoring said lead within an epidural space of a vertebrum of a spine, said elongate member being positioned entirely within the hollow lead body in its retracted state, and being extendible outwardly from its position within the hollow lead body through said port.

2. The lead of claim 1 wherein said laterally extending vertebrum engaging means comprise at least one pair of vanes or tines which extend laterally outwardly from the lead body.

3. The lead of claim 2 wherein said laterally extending vertebrum engaging means comprise two pairs of vanes which extend laterally outwardly from the lead body opposite each other.

4. The lead of claim 3 wherein said laterally extending vertebrum engaging means are located on said lead body distal end portion just proximal to said sleeve electrode.

5. The lead of claim 2 wherein said vanes are made of elastomeric material.

6. The lead of claim 2 wherein said vanes are made of polyurethane.

7. The lead of claim 1 wherein said elongate member comprises a tine.

8. The lead of claim 7 wherein said tine is made of polyurethane.

9. The lead of claim 7 wherein said tine is made of a elastomeric material.

10. The lead of claim 7 wherein said electrode assembly has a lumen therein and said tine is longitudinally located in its retracted state within said lumen of said distal electrode assembly.

11. The lead of claim 10 wherein said tine distal end is rounded.

12. The lead of claim 10 wherein said sleeve electrode has said port therein and said tine is extendible outwardly from its position the lumen through said port in said electrode sleeve.

13. The lead of claim 12 wherein said port is machined into said electrode sleeve.

14. The lead of claim 12 wherein said port is positioned on a dorsal forming surface of said lead.

15. The lead of claim 12 wherein said sleeve electrode has an internal annular shoulder with a beveled portion adjacent said port and said distal end of said tine abuts and slides upwardly along said beveled portion and out of said port when actuated.

16. The lead of claim 7 including an actuating cable which is bonded at its distal end to said proximal inner end of said tine which is located in said lead body forwardly of said port.

17. The lead of claim 16 wherein said actuating cable extends through said lead body and outwardly from the proximal end of said lead body.

18. The lead of claim 16 wherein said proximal end of said actuating cable extends outwardly from the proximal end of said lead body and is capable of being pulled outwardly from said proximal end of said body to pull the proximal end of said tine proximally to force the distal end of said tine outwardy through said port and against the dorsal surface of a vertebrum.

19. The lead of claim 1 wherein said tine is elongate and has slightly curved configuration adjacent said free end thereof.

20. A method of using a neural stimulatng lead with an active fixation stabilizing mechanism comprising the steps of: feeding a lead comprisng a hollow lead body having a proximal end and a distal end portion which has a side port therein, a distal electrode assembly mounted in said distal end portion and including a sleeve electrode, a stimulator connector mounted at said proximal end of said lead body, a wire conductor connected between said sleeve electrode and said stimulator connector and an active fixation stabilizing mechanism situated in said distal end portion and comprising, stiff but flexible, laterally projecting, vertebrum engaging means and extendable/retractable, dorsal stabilizing means comprising a stiff, but flexible, elongate member which has a proximal inner end and a distal free end and which is movable transversely of said vertebrum engaging means through said port between a retracted position and an extended position where said free end bears against a dorsal wall of a vertebrum for anchoring said lead within an epidural space of a vertebrum of a spine, said elongate member being positioned entirely within the hollow lead body in its retracted state, and being extendible outwardly from its position within the hollow lead body through said port, through an incision and into an epidural space or foramen of a vertebrum in such a manner that said laterally extending vertebrum engaging means lie in a horizontal plane when a patient is supine and such that said elongate member can be moved upwardly within the foramen; positioning said sleeve electrode in a proper position; and once said sleeve electrode is positioned, moving said elongate member an appropriate distance upwardly and outwardly of said lead body to place the distal free end of said elongate member at a position where said distal end engages and anchors itself against a dorsal wall of the vertebrum within which is it positioned.

* * * * *

UNITED STATES PATENT AND TRADEMARK OFFICE
CERTIFICATE OF CORRECTION

PATENT NO. : 4,590,949

DATED : May 27, 1986

INVENTOR(S) : Peter J. Pohndorf

It is certified that error appears in the above-identified patent and that said Letters Patent is hereby corrected as shown below:

Column 1, line 10, "tne" should be --the--.

Column 3, line 43, "29" should be --39--.

Column 6, line 23, "position the" should be --position within the--.

Signed and Sealed this

Twenty-fourth Day of February, 1987

Attest:

DONALD J. QUIGG

Attesting Officer
Commissioner of Patents and Trademarks